Figure 1:

United States Patent [19]

Mauri

[11] Patent Number: 4,511,510
[45] Date of Patent: Apr. 16, 1985

[54] PROCESS FOR PREPARING A 7-CHLORO-5-(2-CHLOROPHENYL)-BENZODIAZEPINONE

[75] Inventor: Francesco Mauri, Monza, Italy

[73] Assignee: Ravizza S.p.A., Milan, Italy

[21] Appl. No.: 952,397

[22] Filed: Oct. 18, 1978

[30] Foreign Application Priority Data

Oct. 18, 1977 [IT]  Italy ............................... 28738 A/77

[51] Int. Cl.³ ........................................... C07D 243/32
[52] U.S. Cl. ............................................. 260/239.3 D
[58] Field of Search ................................. 260/239.3 D

[56] References Cited

U.S. PATENT DOCUMENTS 3,781,390 12/1973 Topliss .......................... 260/239.3 D

FOREIGN PATENT DOCUMENTS 1056289 1/1967 United Kingdom ........... 260/326 N
1063891 4/1967 United Kingdom ........ 260/239.3 D Primary Examiner—Robert T. Bond Attorney, Agent, or Firm—Stevens, Davis, Miller & Mosher

[57] ABSTRACT

A process for preparing 7-chloro-5-(2-chlorophenyl)-1,3-dihydro-2H-1,4-benzodiazepin-2-one of the formula:

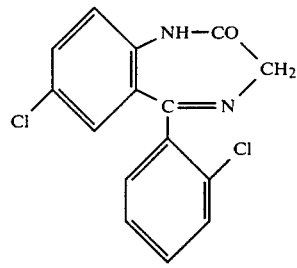

utilizing 2′,5-dichloro-2-aminobenzophenone, phthalimidoglycine and hydrazine in a single passage and in a single reaction medium under critical reaction conditions.

4 Claims, 4 Drawing Figures

PROCESS FOR PREPARING A 7-CHLORO-5-(2-CHLOROPHENYL)-BENZODIAZEPINONE

This invention relates to a new industrial process for preparing 7-chloro-5-(2-chlorophenyl)-1,3-dihydro-2H-1,4-benzodiazepin-2-one in an extremely simple and economical manner.

BACKGROUND

7-Chloro-5-(2-chlorophenyl)-1,3-dihydro-2H-1,4-benzodiazepin-2-one is a compound of the formula:

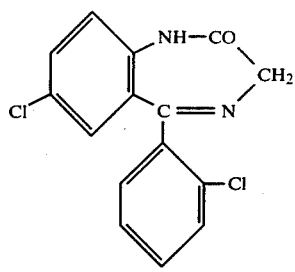
(I)

This compound (I) has been known by its chemical structure for many years but it has been studied pharmacologically and clinically in depth only recently and these studies have shown that it possesses an activity far exceeding that of the best known benzodiazepines already commercially available.

This has given rise to a need for finding an industrial process by which this compound can be produced in pharmaceutical purity in an economically acceptable manner.

It is known from British Pat. No. 1,063,891 that a limited group of benzodiazepinones comprising in particular a phenyl group non-substituted in position 5, can be prepared by hydrazinolysis of a phthalimidoacetamide of the formula:

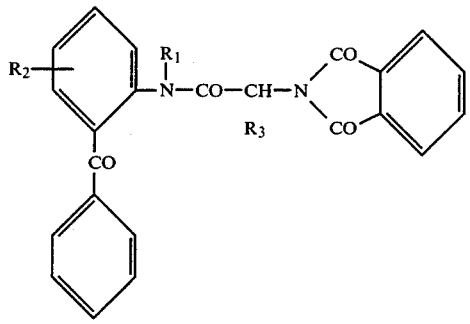

in which $R_1$ is hydrogen, methyl or ethyl; $R_2$ is halogen and $R_3$ is hydrogen, alkyl, phenyl or p-hydroxybenzyl.

THE INVENTION

This process proceeds in an acceptable time and in acceptable yield only if the reactants are reacted in ethanol under reflux.

It has now been discovered that the compound 7-chloro-5-(2-chlorophenyl)-1,3-dihydro-2H-1,4-benzodiazepin-2-one can be prepared from 2',5-dichloro-2-aminobenzophenone and phthalimidoglycine with hydrazine, probably by passing through the intermediate phthalimidoacetamide derivative in a single passage, in a single reaction medium without separarting intermediate products and under absolutely critical solvent and temperature conditions.

The subject compound (I) cannot be prepared in an industrially acceptable yield outside the discovered reaction conditions or, in particular, under conditions heretofore utilized for the preparation of other benzodiazepinones because it is not possible to carry out such processes in a single passage using small solvent volumes, nor is it possible to separate out the subject product (I) from resulting by-products at high purity and with high yields.

The process of this invention is based on the following reaction mechanism:

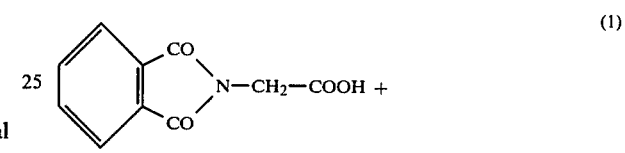
(1)

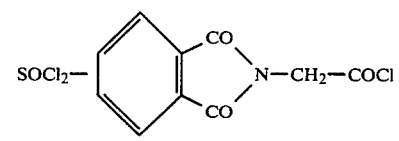

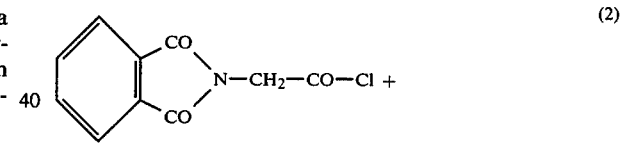
(2)

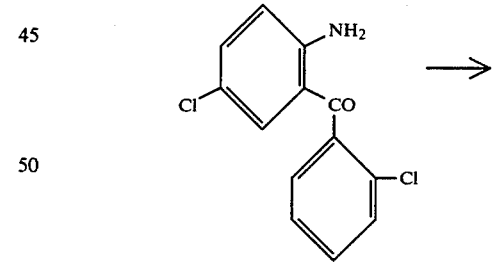

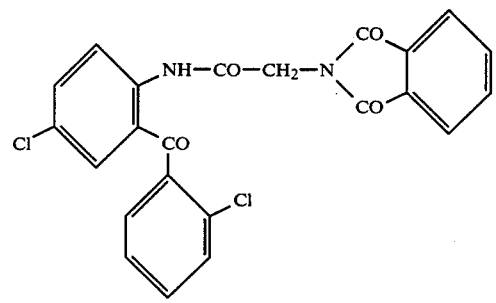

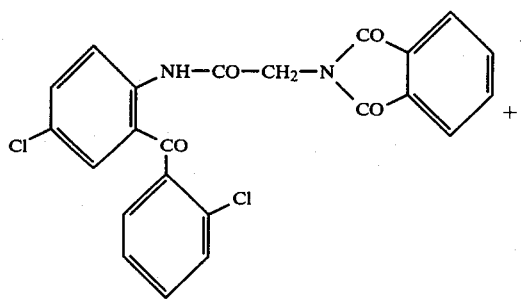

Stages (1) and (2) of the reaction are carried out by heating in a chloroform solution, whereas, stage (3) is carried out in a chloroform and ethanol solution at ambient temperature.

The thionyl chloride is added to the phthalimidoglycine either in stoichiometric amounts or in a slight excess not exceeding ten percent. The 2',5-dichloro-2-aminobenzophenone must be used in slight deficiency relative to the initial phthalimidoglycine. The hydrazine is used in a 2:1 ratio relative to the aminobenzophenone.

It is absolutely critical to this process that stage (3) be carried out with a 2',5-dichloro-2-aminobenzophenone:chloroform:ethanol ratio of 1:15–16:4–5 by weight and at ambient temperature.

As stated above, the process of this invention cannot be carried out economically outside of the herein-specified range of reaction conditions and certainly not on an industrial scale.

The product of this process, 7-chloro-5-(2-chlorophenyl)-1,3-dihydro-2H-1,4-benzodiazepin-2-one (I), is active on the central nervous system, on which it demonstrates a truly exceptional activity both as an anxiolytic and as a hypnoinducer. In addition, this new benzodiazepinone (I) has found wide use in the neuropsychiatric field in curing psychotic symptoms of average gravity.

To demonstrate the importance of this benzodiazepinone and the importance of its industrial production, some pharmacologically significant data is given hereinafter in comparison with equivalent data for the best benzodiazepinones now available commercially.

TABLE 1

Comparative data on the pharmacological activity of some benzodiazepines in the mouse, expressed as $DE_{50}$ (mg/Kg/ca)

| | Rota Red | Foot shock | Anti metrazole | Anti ES Max |
|---|---|---|---|---|
| *Chlorodiazepoxide | 31 | 40 | 8 | 40 |
| *Oxazepam | 7 | 40 | 0.7 | 28 |
| *Diazepam | 6 | 10 | 2 | 22 |
| *Flurazepam | 6 | 20 | 2 | 82 |
| °Demethyldiazepam | 4 | 20 | 1 | 19 |
| *Chlorodemethyldiazepam | 1 | 2 | 0.9 | 0.9 |

*Randall L. O. et al. in: Psychopharmacological agents (Vol. III) Gordon M. (Ed.), Academic Press New York, 1974, pag. 175–281
°Randall L. O., Scheckel C. L. and Banzinger R. F. (1965 B). Pharmacology of the metabolites of chlorodiazepoxide and diazepam. Current therapeutic research 7: 590–606

TABLE 2

$DL_{50}$ of the main benzodiazepines mg/Kg

| | Mouse | | Rat |
|---|---|---|---|
| Benzodiazepine | OA | I.P. | OA |
| Chlorodiazepoxide | 720 | 268 | 2000 |
| Diazepam | 720 | 220 | 1240 |
| Demethyldiazepam | 1300 | 670 | >5200 |
| Oxazepam | >4000 | 800 | >8000 |
| Flurazepam | 870 | 290 | 1232 |
| Chlorodemethyldiazepam | 1100 | 1100 | 2000 |

The data in this table is taken from "Tavole degli psicofarmaci" by S. Del Mastro, V. Gallo, P. L. Morselli - Geigy documentation - 1975

Many clinical case studies confirm the relationship between activity and toxicity in comparisons with other benzodiazepines at the pharmacological level.

A practical example of the process of this invention is set forth below.

EXAMPLE

Phthalimidoglycine (14 kg), chloroform (80 kg) and pyridine (0.5 kg) are refluxed under agitation in a 250 liter enamelled reactor.

Thionyl chloride is added slowly and the mixture is kept under reflux until a clear solution forms.

The resulting clear solution is cooled and 2',5-dichloro-2-aminobenzophenone (17 kg) is added slowly so as to avoid any over-development of hydrogen chloride.

When hydrogen chloride is no longer evolved the reaction is completed with gentle heating. Water (80 kg) is added, the aqueous layer is separated and the operation is twice repeated.

94% Ethanol (75 kg), chloroform (180 kg) and hydrazine hydrate (5.6 kg) are added to the residual chloroform solution.

The mixture is agitated at ambient temperature for one night and the resulting phthylhydrazine is centrifuged and evaporated to dryness.

To isolated the 7-chloro-5-(2-chlorophenyl)-1,3-dihydro-2H-1,4-benzodiazepin-2-one (I) at pharmaceutical purity, the residue is taken up with chloroform (120 kg) at ambient temperature, the mixture is filtered and the filtrate is treated with 3N hydrochloric acid (80 liter) under agitation and with cooling.

The perfectly crystalline, pure hydrochloride of the product (I) is separated by centrifuging and is washed with acetone (10 liter). The yield is practically quantitative with respect to the 2',5-dichloro-2-aminobenzophenone reactant.

To obtain the product as a free base the following procedure is adopted: The hydrochloride is suspended in ethanol (50 liter) and the suspension is neutralized with ammonia. Water (50 liter) is then added slowly and the perfectly crystalline product (I) is allowed to separate.

This product (I) is centrifuged, washed with water and dried to afford 18.2 kg of 7-chloro-5-(2-chlorophenyl)-1,3-dihydro-2H-1,4-benzodiazepin-2-one (equal to a yield of 95 percent on the initial benzophenone) having the following characteristics:

| Elementary Analysis: | C | H | N |
|---|---|---|---|
| Calculated: | 59.50 | 3.27 | 9.18 |
| Found: | 59.27 | 3.14 | 9.16 |

Melting Point: 200°–202° C.

UV Spectrum: See FIG. 1; a characteristic maximum at 285.

Figure 2:
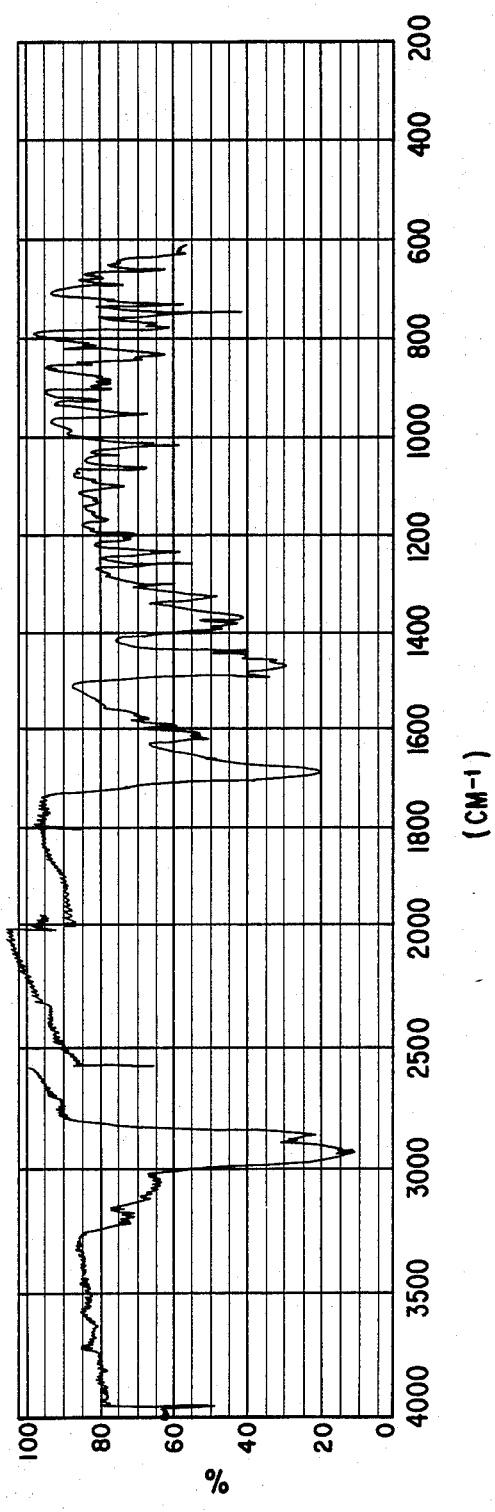

IR Spectrum: See FIG. 2; the IR Spectrum was carried out in Nujol.

Figure 3:
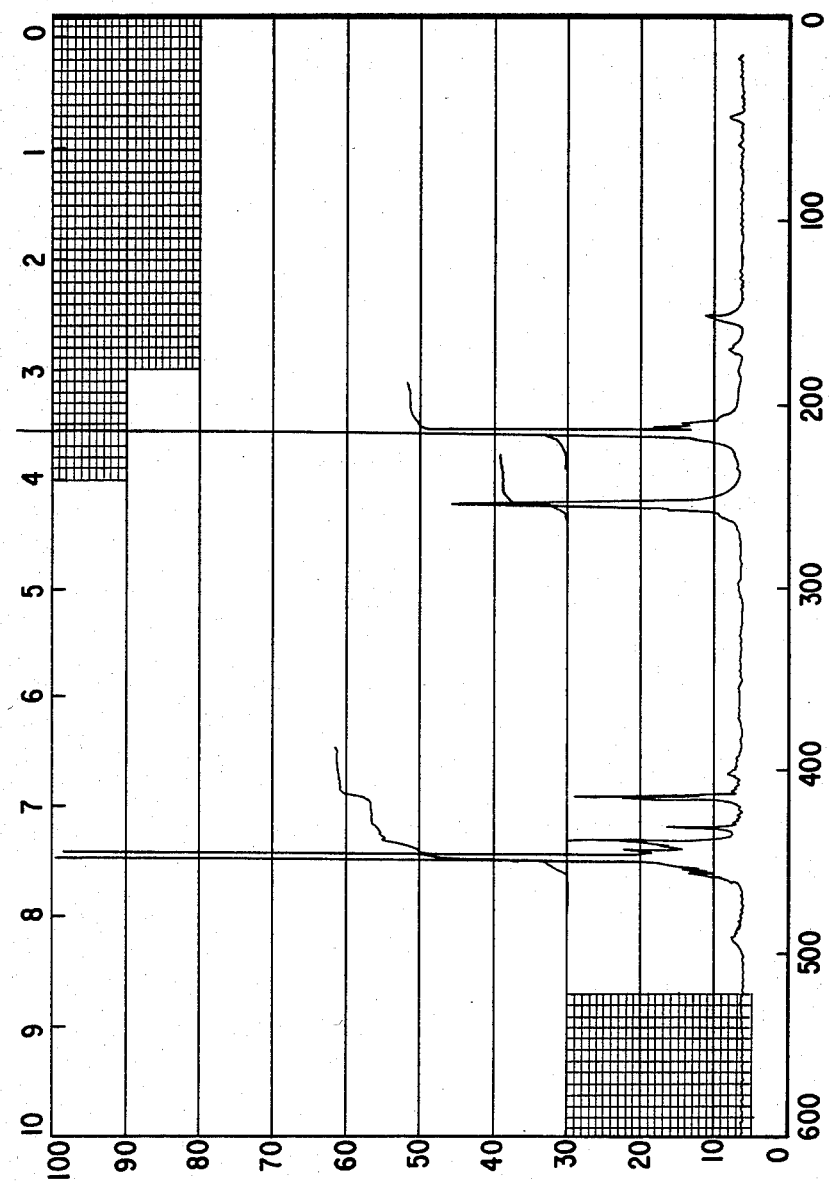

NMR Spectrum: See FIG. 3.

Figure 4:
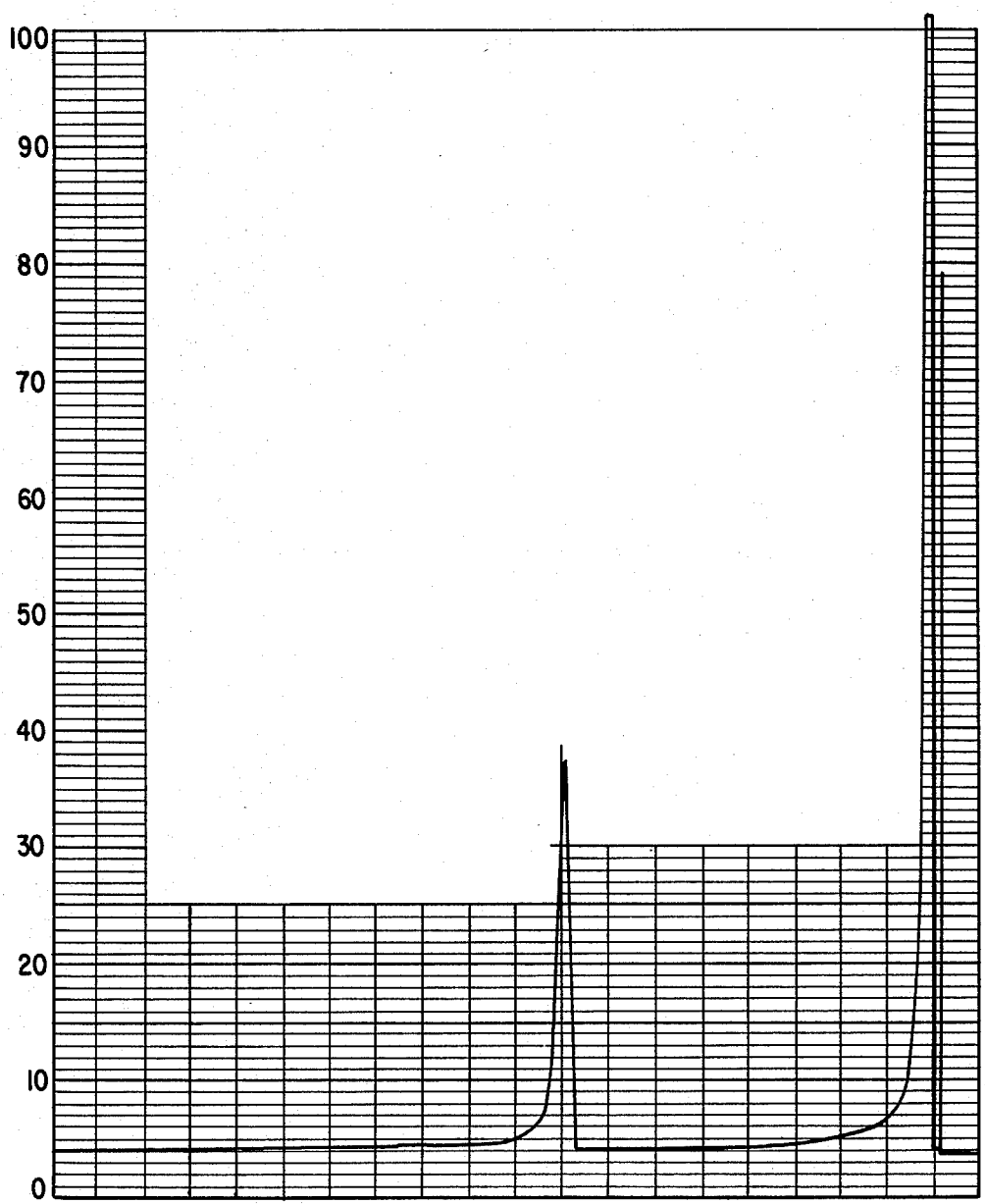

The absolute purity of the product was demonstrated by means of gas chromatography and thin layer chromatography:

Gas Chromatogram: See FIG. 4 in which only one peak is shown.

Thin Layer Chromatography:
Silica gel support.
Eluent: benzene/ethyl acetate 1:1.
Detector $UV_{254}$.
Rf 0.45.

For application up to 500, there is only one spot.

What is claimed is:

1. A method for preparing 7-chloro-5-(2-chlorophenyl)-1,3-dihydro-2H-1,4-benzodiazepin-2-one in a single passage and in a single reaction medium, without the separation of intermediate compounds, which comprises refluxing a suspension of phthalimidoglycine in chloroform with thionyl chloride until a clear solution forms; first adding to said clear solution 2',5-dichloro-2-amino-benzophenone and, thereafter, adding ethanol, chloroform and hydrazine hydrate under ambient temperature conditions to obtain the desired product, the ratio by weight of 2',5-dichloro-1-aminobenzophenone to chloroform to ethanol being 1:15–16:4–5, and the molar ratio of 2',5-dichloro-2-aminobenzophenone to hydrazine being approximately 1:2.

2. The method of claim 1 wherein the thionyl chloride and phthalimidoglycine are employed in stoichiometric amounts.

3. The method of claim 1 wherein the concentration of thionyl chloride with respect to phthalimidoglycine is slightly in excess of stoichiometric amounts.

4. The method of claim 5 wherein the excess of thionyl chloride over phthalimidoglycine does not exceed ten percent.

* * * * *